(12) United States Patent
Johnston, III et al.

(10) Patent No.: US 12,042,125 B2
(45) Date of Patent: Jul. 23, 2024

(54) ENDOSCOPIC SHEATH HOLDING TIP AND STABILIZATION SYSTEM

(71) Applicant: Mediflex Surgical Products, LLC, Islandia, NY (US)

(72) Inventors: William K. Johnston, III, Northville, MI (US); Daniel Adler, Oyster Bay, NY (US); Steven Culver, Stony Brook, NY (US); Joan L. Carter, Levittown, NY (US); John M. Sfakis, Mount Sinai, NY (US)

(73) Assignee: MEDIFLEX SURGICAL PRODUCTS, LLC, Islandia, NY (US)

( * ) Notice: Subject to any disclaimer, the term of this patent is extended or adjusted under 35 U.S.C. 154(b) by 787 days.

(21) Appl. No.: 17/154,530

(22) Filed: Jan. 21, 2021

(65) Prior Publication Data
US 2022/0225863 A1 Jul. 21, 2022

(51) Int. Cl.
*A61B 1/00* (2006.01)
(52) U.S. Cl.
CPC ...... *A61B 1/00149* (2013.01); *A61B 1/00135* (2013.01)
(58) Field of Classification Search
CPC ............ A61B 1/00112; A61B 1/00135; A61B 1/00149; A61B 90/50; A61B 90/57; A61B 2090/571
See application file for complete search history.

(56) References Cited

U.S. PATENT DOCUMENTS

| | | |
|---|---|---|
| 4,867,404 A | 9/1989 | Harrington et al. |
| 5,224,680 A | 7/1993 | Greenstein et al. |
| 2007/0185376 A1* | 8/2007 | Wilson ................. A61B 90/57 600/102 |

OTHER PUBLICATIONS

European Search Report issued in European Application No. EP22152150.3, Dated Jun. 14, 2022, pp. 1-9.

\* cited by examiner

*Primary Examiner* — Timothy J Neal
(74) *Attorney, Agent, or Firm* — Tutunjian & Bitetto, P.C.

(57) ABSTRACT

An endoscopic sheath holding tip and stabilization system is configured to be connected to a table mounted flexible or rigid arm or other surgical support device used over the patient during a surgical procedure. The sheath holder includes a hook structure configured to engage the underside of the scope sheath (e.g., inflow and outflow ports), while a plunger mechanism engages the top surface of the sheath. The downward pressure of the plunger mechanism working against the upward forces of the hook structure operate to stabilize the scope sheath without requiring user intervention. In this manner, the scope and other instruments can be introduced into the stabilized scope sheath without requiring user assistance to hold the scope once positioned in the stabilized sheath.

9 Claims, 11 Drawing Sheets

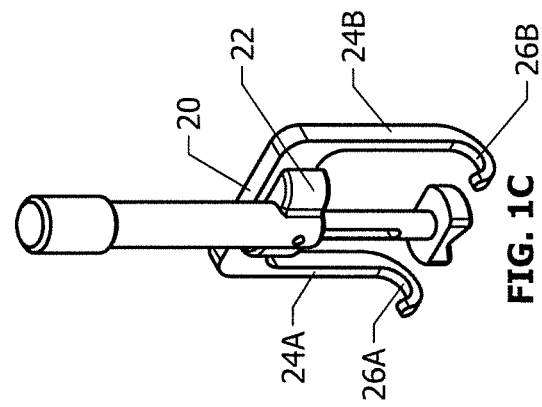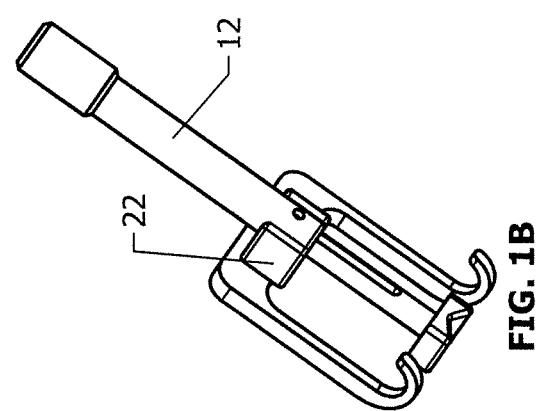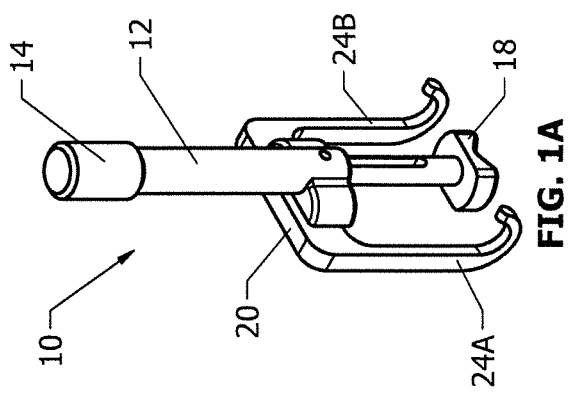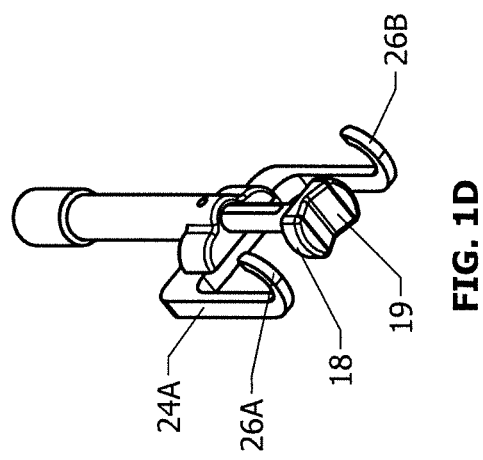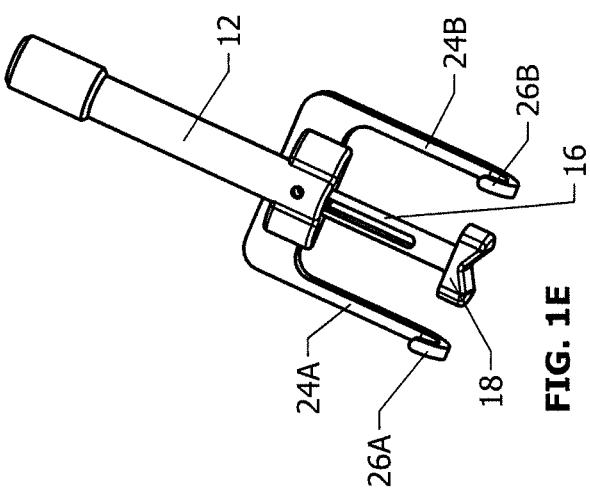

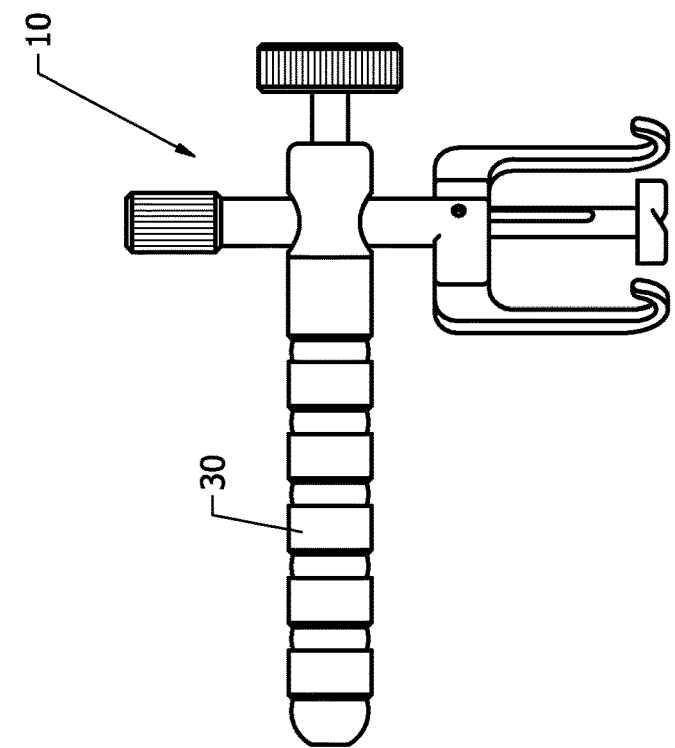
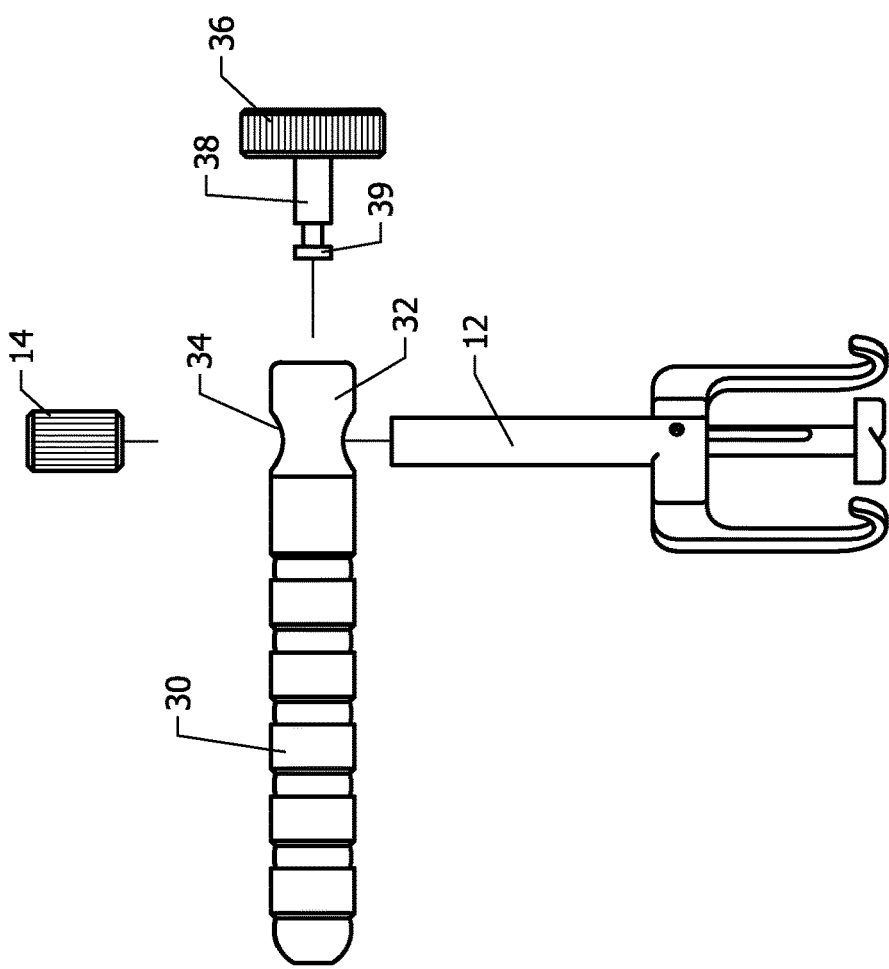
FIG. 3A
FIG. 3B

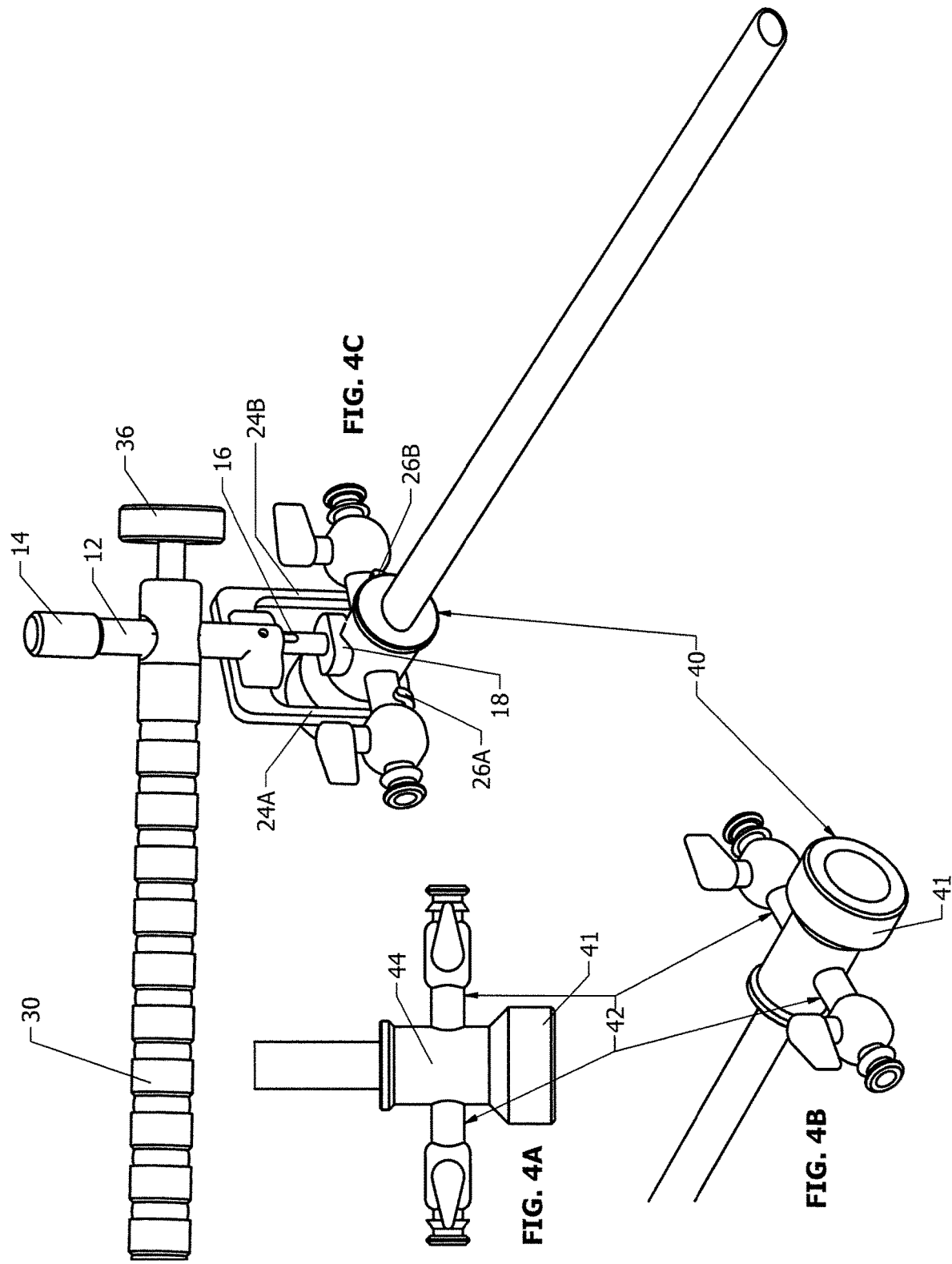

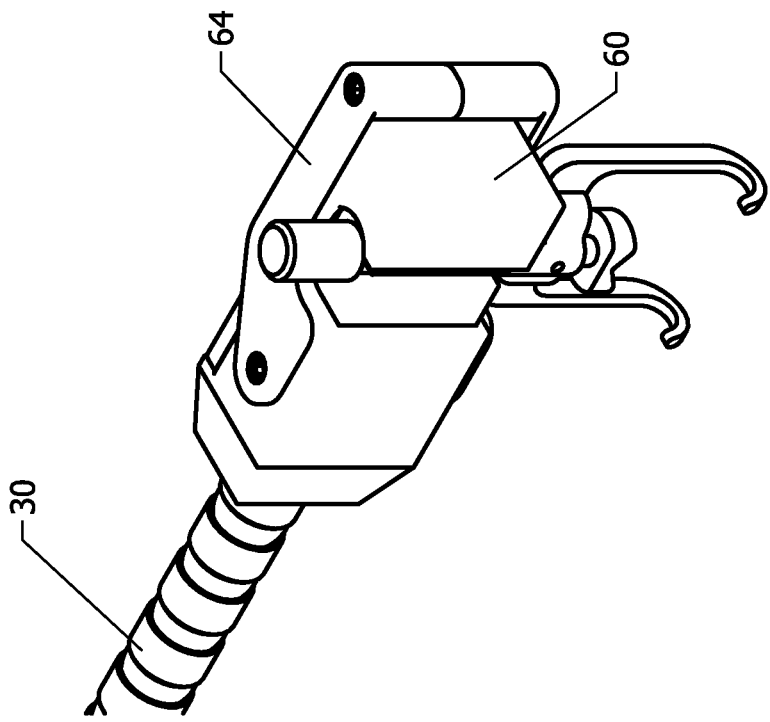
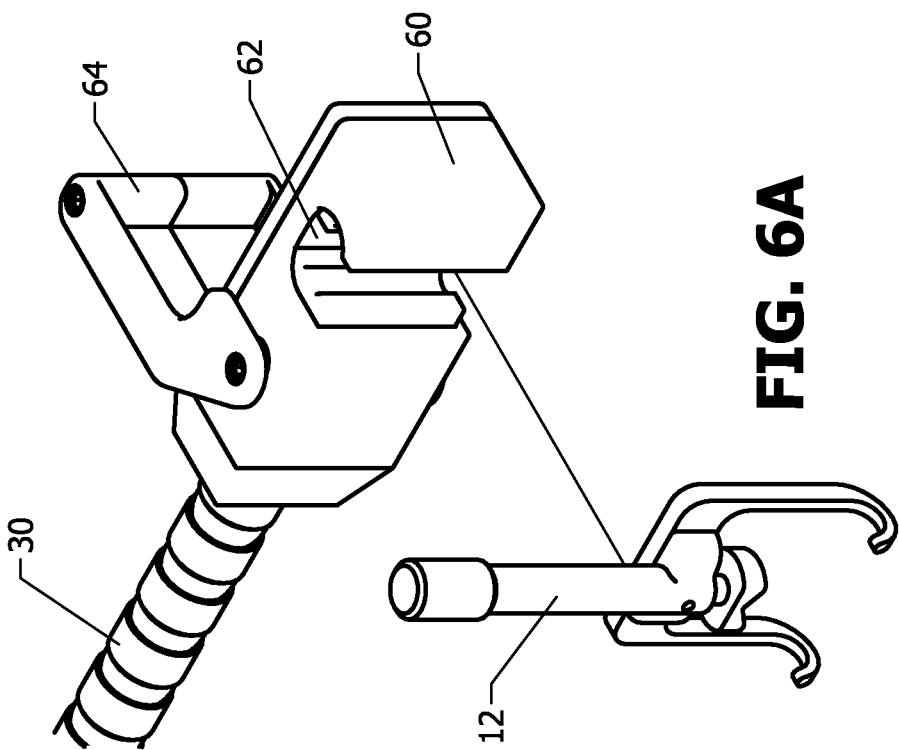

ENDOSCOPIC SHEATH HOLDING TIP AND STABILIZATION SYSTEM

BACKGROUND

Technical Field

The present invention relates to the use of a scope such as a cystoscope or endoscope. More particularly, it relates to a device for holding, securing and stabilizing a scope sheath in place during a surgical procedure.

Description of the Prior Art

By way of example, when a urologist operates on a patient in the dorsal lithotomy position, they must share the narrowed space between the patient's legs or place the assist in an ergonomically challenging position of holding the cystoscope sheath over the patient's leg, all while holding the cystoscope sheath in the correct, static position while trying to hand the surgeon wires, stents, syringes, or other devices. For difficult anatomy (e.g., large median prostatic lobes, severely trabeculated bladders, bleeding etc.), it may require the surgeon to manipulate a wire (instrument or device) with two hands yet maintain visualization of the ureteral orifice.

What is less apparent or less discussed, is how stressful it can be for the scrub to assist the surgeon during these types of procedures, especially in difficult, long cases or when they have minimal experience with urological procedures.

Radiation exposure is another concern. The urologist's hands that hold the cystoscope sheath are more prone to exposure of harmful radiation during fluoroscopic imaging. The doctor's assistant is also at risk for radiation exposure when holding the cystoscope sheath. Since radiation exposure reduces exponentially when moving away from the same, a foot or two can make a substantial difference in what the operating room personnel is exposed to as a result.

It is therefore desirable to remove the need for a scrub nurse or doctor or anyone in the operating room to hold the cystoscope sheath during the performance of surgical procedures.

SUMMARY OF THE INVENTION

This and other aspects of the invention are achieved by an endoscopic sheath holding tip and stabilization system that includes a table mounted flexible or rigid arm engaging portion configured securely attach the stabilization system to a table mounted flexible or rigid arm. An a scope sheath engaging portion configured to engage a scope sheath from an underside thereof and an upper surface thereof to secure the scope sheath from any movement once positioned in the scope sheath engaging portion.

According to another embodiment, the scope sheath stabilization system includes a table mounted flexible or rigid arm engaging portion configured to securely attach the scope sheath and holding tip to the table mounted flexible or rigid arm, and a scope sheath engaging portion configured to engage and secure the scope sheath from any movement once positioned in the scope sheath engaging portion.

In one embodiment, the scope sheath engaging portion includes an inverted U shape device having a top portion connected to the table mounted flexible or rigid arm engaging portion and two downward extending legs. Each leg has a hook positioned at a bottom thereof configured to be positioned under and engage an underside of the scope sheath. A plunger mechanism extending downward from the top portion engages the upper surface of the scope sheath.

Other aspects and features of the present principles will become apparent from the following detailed description considered in conjunction with the accompanying drawings. It is to be understood, however, that the drawings are designed solely for purposes of illustration and not as a definition of the limits of the present principles, for which reference should be made to the appended claims. It should be further understood that the drawings are not necessarily drawn to scale and that, unless otherwise indicated, they are merely intended to conceptually illustrate the structures and procedures described herein.

BRIEF DESCRIPTION OF THE DRAWINGS

In the drawings wherein like reference numerals denote similar components throughout the views:

FIGS. 1A-1E show various views of the endoscopic sheath holding tip and stabilization system according to an embodiment of the invention;

FIG. 3A shows a dissembled view of the scope sheath and holding tip stabilization system with an exemplary table mounted flexible or rigid arm according to an embodiment of the invention;

FIG. 3B shows an assembled view of the scope sheath and holding tip stabilization system with an exemplary table mounted flexible or rigid arm according to an embodiment of the invention;

FIGS. 4A and 4B show a top view and rear perspective view, respectively, of a cystoscope sheath according to an embodiment of the invention;

FIG. 4C is a perspective view of scope sheath and holding tip stabilization system with cystoscope sheath positioned/stabilized therein, according to an embodiment of the invention;

FIGS. 6A and 6B show an alternative connection method between the table mounted flexible or rigid arm and the scope sheath and holding tip stabilization system according to another embodiment of the invention;

DETAILED DESCRIPTION

Figure 1F:
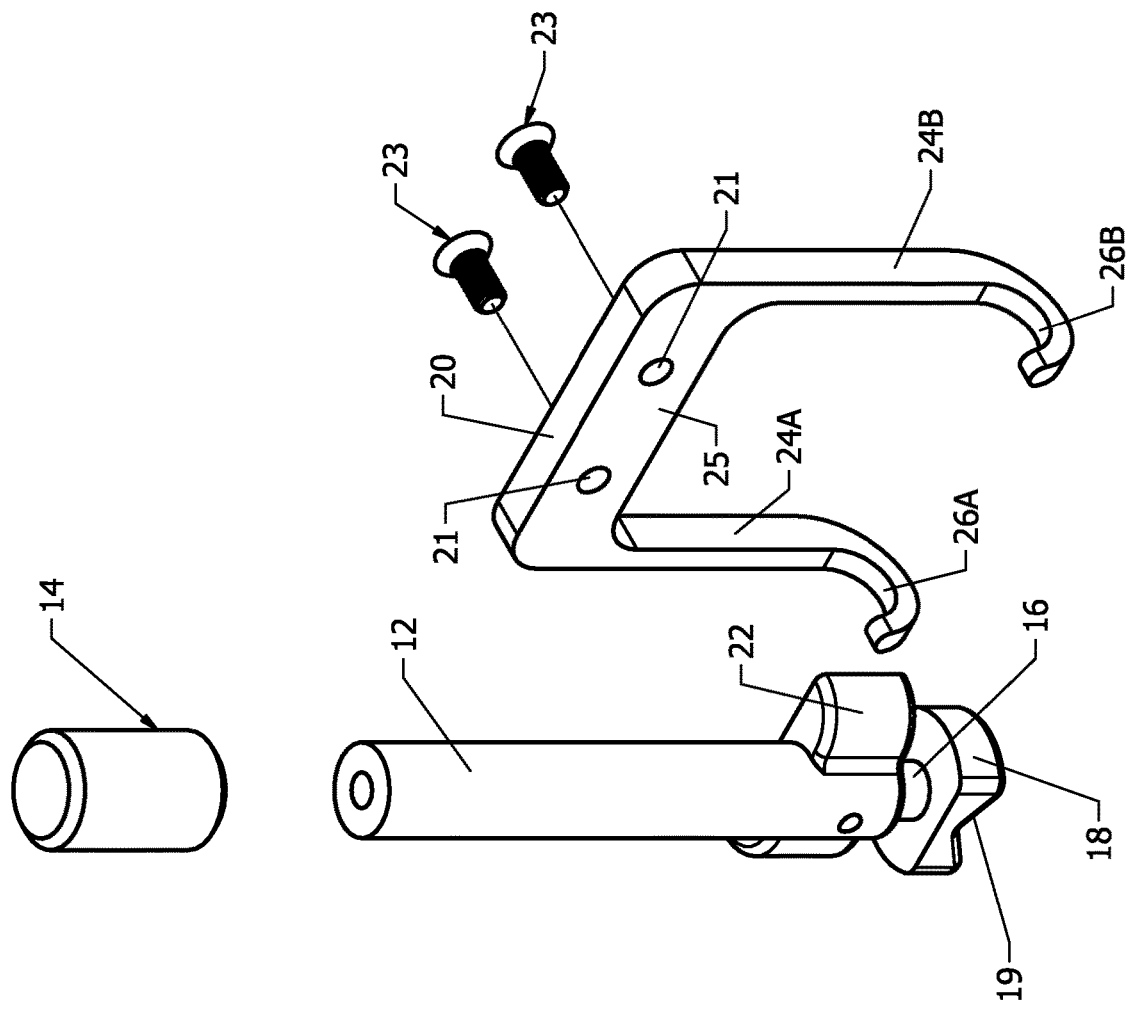
FIG. 1F is an exploded view of the scope sheath and holding tip stabilization system according to an embodiment of the invention.

Referring to FIGS. 1A-1F, there is shown the endoscopic sheath holding tip and stabilization system 10 (hereinafter referred to as the "sheath holder" 10) according to an embodiment of the invention. In this embodiment, the sheath holder 10 includes a sheath engaging portion 20 which include a sheath engaging plunger assembly 16, 18, 19, and a table mounted flexible or rigid arm connection portion consisting of a shaft 12 that (as will be described in further detail below) houses the shaft 16 of the sheath engaging plunger assembly. At a top end of shaft 12 is a safety knob 14 that operates to serve as a safety measure to ensure the sheath holder does not fall completely out of the flexible or rigid arm if not secured properly. In this embodiment, the sheath engaging portion 20 has a generally upside down or inverted U shape with a central upper portion 25, and two downwardly extending legs 24A and 24B. At the bottom of each leg 24A and 24B is a hook 26A and 26B, respectively, that is configured to engage and hold onto the scope sheath inflow and outflow ports.

At the base of the shaft 12 of table mounted flexible or rigid arm connection portion are included one or more connection points 22 that are configured to receive screws 23 which pass through holes 21 in the sheath engaging portion 20 (see FIG. 1F). In this manner, the bottom of shaft 12 is connected to the central upper portion 25 of the sheath engaging portion 20 as shown. Within the shaft 12 is positioned a slidable and spring biased plunger 16 having a foot 18 and which foot 18 includes a beveled or curved surface 19. The beveled or curved surface 19 of foot 18 can take many different shapes/forms to ensure its engagement with the upper surface of the sheath is secure from any movement once so engaged. For example, an inverted V-shape has proven to work very well when engaging cylindrical sheath shapes as that shown. Those of skill in the art will appreciate that variations in the shape of foot 19 can be made without departing from the intended scope of the invention. Plunger 16 with foot 18 is preferably spring biased downward.

In accordance with other embodiments, the plunger 16 could be manually locked into place once the foot 18 is positioned against the upper surface of the sheath. Any suitable locking mechanism could be used, including, for example, a transverse locking screw passing through the shaft 12 and engaging an internal side of the plunger 16. Another example could include a one direction or one-way ratcheting mechanism with a release, such that when the plunger 16 would be pressed downward against the sheath, a ratcheting mechanism inside the shaft 12 would include teeth that a ratchet pawl on the plunger would engage and lock into at each downward increment until locked against the sheath surface. A ratchet pawl release would allow for removal of the plunger against the sheath.

According to one preferred implementation, the table mounted flexible arm or rigid arm connection portion (e.g., the shaft 12) is made of surgical steel. The sheath engaging portion 20 is also preferably made from surgical steel. In other applications or uses, the material the device of the present invention can be made from could also include one or more of titanium, aluminum and/or plastics of various types.

Figure 2A:
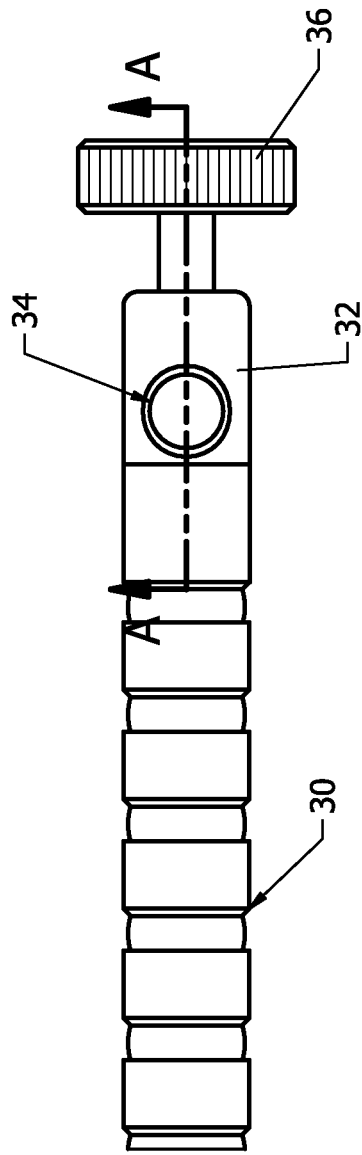
FIG. 2A shows a side view of an exemplary table mounted flexible or rigid arm to which the scope sheath and holding tip stabilization system is attached according to an embodiment of the invention.
Figure 2B:
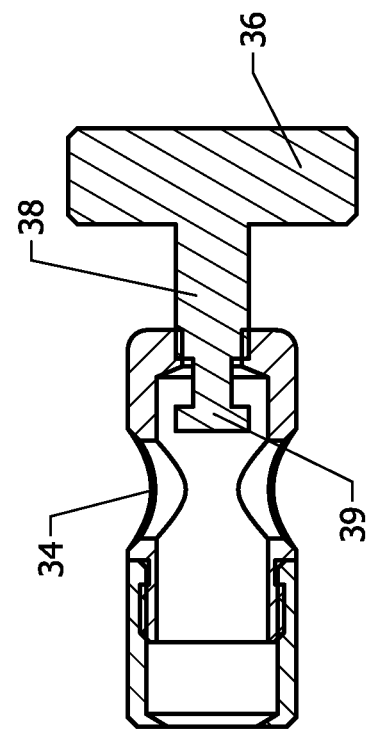
FIG. 2B is a cross-sectional view of the exemplary table mounted flexible or rigid arm of FIG. 2A, taken along lines A-A thereof.

FIGS. 2A and 2B show an example of a table mounted flexible arm 30 having an end 32 that includes a hole or aperture 34 therein. A securing knob 36 has a shaft 38 with an end 39 that is in communication with the aperture 34 such that tightening of the securing knob causes the end 39 to engage shaft 12 of the sheath holder 10 such that the correct orientation/depth and positioning of the scope sheath (and thereby the scope) can be securely maintained.

Those of skill in the art will appreciate that a table mounted flexible or rigid arm system as described herein is common to a vast array of surgical procedures. These table mounted systems are anchored to a bar or rail that is mounted on the side of the operating table. This bar or rail is commonly used for these types of systems. It is further contemplated herein that the stabilization system for cystoscopy as disclosed herein could have its own dedicated flexible or rigid arm that connects directly to bar or rail on the operating table and can be independent of other table mounted stabilization systems.

FIGS. 3A and 3B show an example of how the shaft 12 engages the aperture 34 of the table mounted flexible arm 30 and is secured in place as described above with reference to FIG. 2.

Figure 5B:
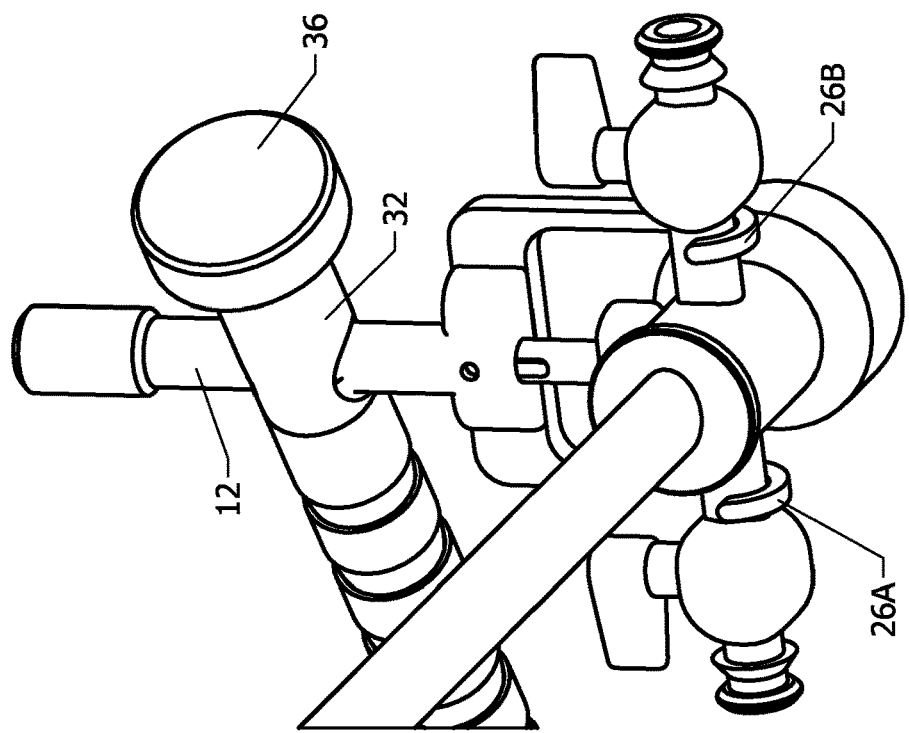
FIGS. 5A and 5B show close of perspective views of the engagement of the scope sheath and holding tip stabilization system with a scope sheath according to the yet another embodiment of the invention.
Figure 5A:
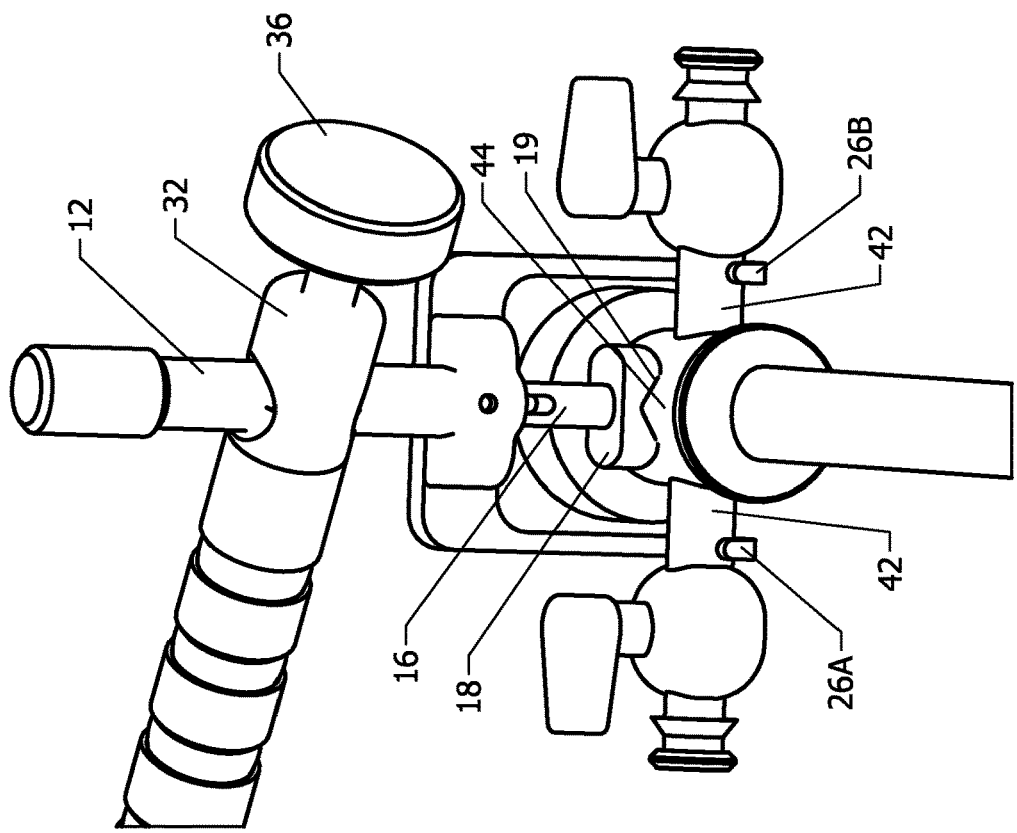

Referring to FIGS. 4A-4C, there is shown a cystoscope sheath 40 having inflow and outflow ports 42, and an upper surface 44. Although shown in FIG. 4C, FIGS. 5A and 5B show enlarged views of how the sheath holder 10 engages and secures to the sheath 40. As shown, the sheath 40 is positioned between the two downwardly extending legs 24A and 24B such that the plunger 16 is pushed upward against its spring bias. The foot 18 with beveled or curved surface 19 engages the upper surface 44 of the sheath. The hooks 26A and 26B hook underneath the inflow and outflow ports 42 as shown.

As will be appreciated from the present disclosure, the spring biased plunger 16 places a downward force on the sheath 40 pressing the same against the stationary hooks 26A and 26B, and thereby operates to completely stabilize the sheath 40. Once stabilized, the position of the sheath 40 is now completely adjustable and capable of being secured in any desired position through the sheath holder as connected to the table mounted flexible arm 30 through shaft 12 and securing knob 36. This now allows for the introduction of the cystoscope (not shown) into the sheath 40 and completely eliminates the need for any personnel to hold or otherwise manually maintain the position of the scope during a surgical procedure.

In accordance with another embodiment, an adjustable ring clamp (not shown) can replace the plunger 16 and hooks 26 as the sheath engaging portion. The ring claim would be configured to fit around the opening 41 of the sheath (see FIGS. 4A and 4B) and locked there around. The ring clamp would be configured to be connected to the table mounted flexible or rigid arm connecting portion in any suitably known manner.

In other embodiments, the configuration of the two hooks 26 and legs 24 could change. For example, rather than hooks 26, the end of legs 24 could converge or be connected together with a cradle like structure configured to be positioned under the opening of the sheath and provide the same upward support that is countered by downward force applied by the plunger mechanism or other upper surface support.

In further embodiments of the invention, the manner in which the sheath holder 10 is connected to the table mounted flexible or rigid arm can be modified without departing from the intended scope and spirit of the invention. By way of example, FIGS. 6A and 6B show a quick grip attachment system 60 positioned at the end of table mounted flexible arm 30. The quick grip attachment system 60 includes a channel or slot 62 configured to receive the shaft 12, and a locking handle 64, that when closed (FIG. 6B) compressed against and secure the shaft 12 in an unmovable fashion in the channel 62.

Figure 7B:
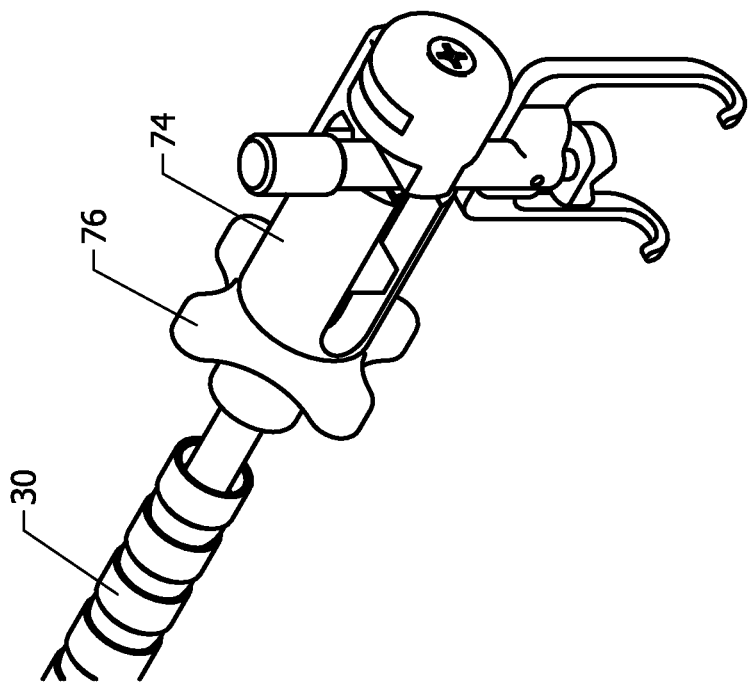
FIGS. 7A and 7B show another connection method between the table mounted flexible or rigid arm and the scope sheath and holding tip stabilization system according to yet another embodiment of the invention.
Figure 7A:
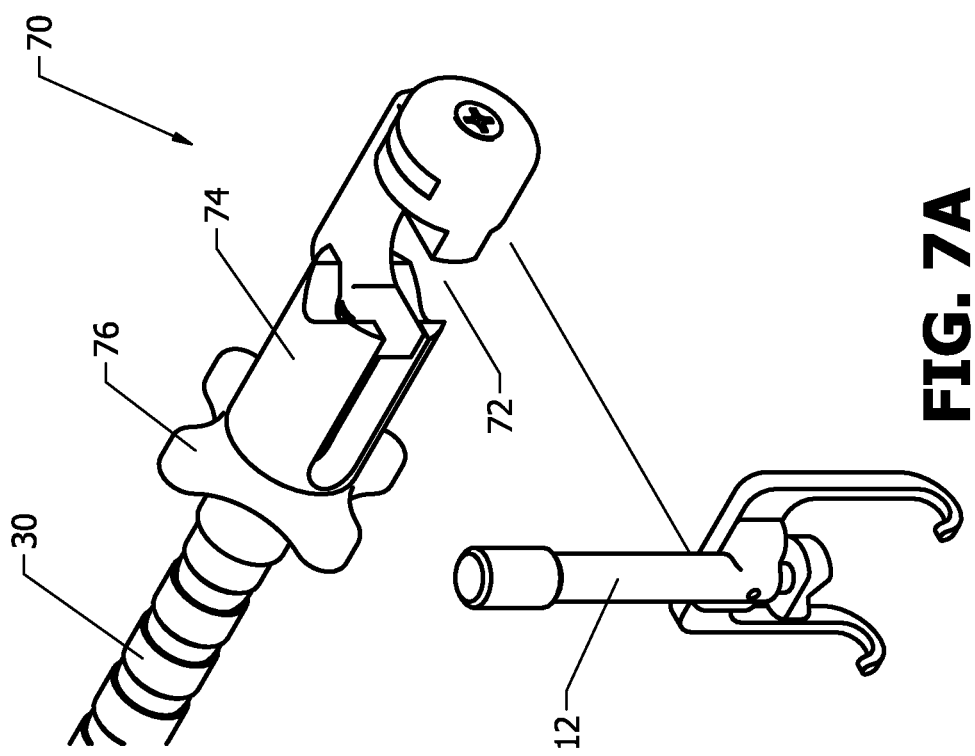

FIGS. 7A and 7B show an anvil attachment style connection mechanism 70 for connecting the sheath holder 10 to the table mounted flexible arm 30 via shaft 12. Here, the connection mechanism includes an opening 72 to receive the shaft 12, and a sliding collar 74 that locks into place with a rotating collar or knob 76. The rotating collar or knob 76 is rotated and translates (via threads not shown) to push and tighten down sliding collar 74 against the shaft 12. In one embodiment a V-shaped feature is included on the rotating collar 74.

Figure 8B:
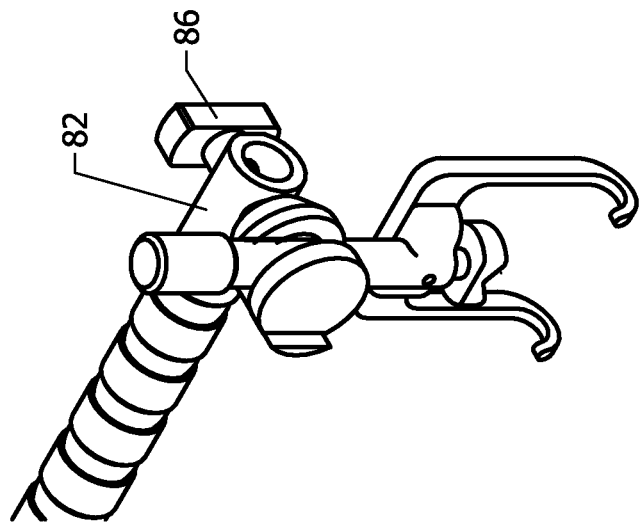
FIGS. 8A and 8B show another connection method between the table mounted flexible or rigid arm and the scope sheath and holding tip stabilization system according to a further embodiment of the invention.
Figure 8A:
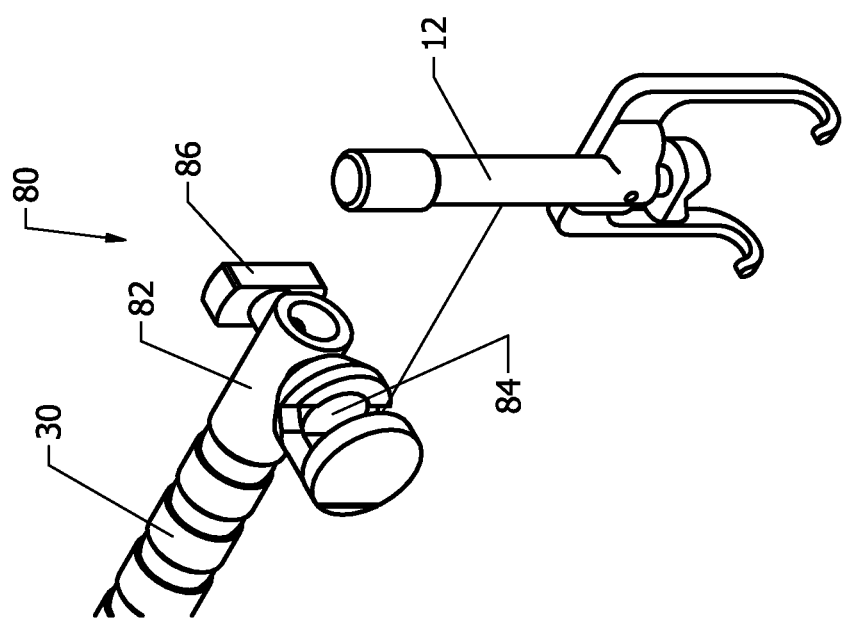

FIGS. 8A and 8B show another anvil attachment style connection mechanism 80 for connecting the sheath holder 10 to the table mounted flexible arm 30 via shaft 12. This connection mechanism includes base 82 that is positioned at the end of the table mounted flexible arm and which includes a receiving channel 84 positioned transverse thereto. A locking knob 86 is internally threaded such that when the shaft 12 is positioned in the receiving channel 84, it can be locked into place using the knob 86 operating like a screw clamp onto the shaft while contained in the channel 84. In accordance with other embodiments, the shaft 12 can include a notch or groove (e.g., V-shaped) that is configured to be engaged by the end of the threaded member controlled by knob 86, which would have a complimentary shape to the notch or groove.

Figure 9B:
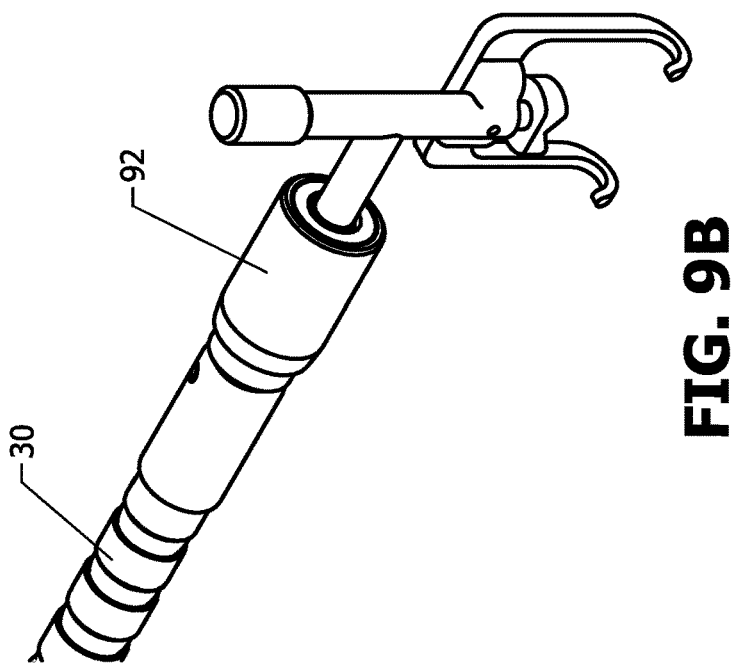
FIGS. 9A and 9B show another connection method between the table mounted flexible or rigid arm and the scope sheath and holding tip stabilization system according to yet another embodiment of the invention.
Figure 9A:
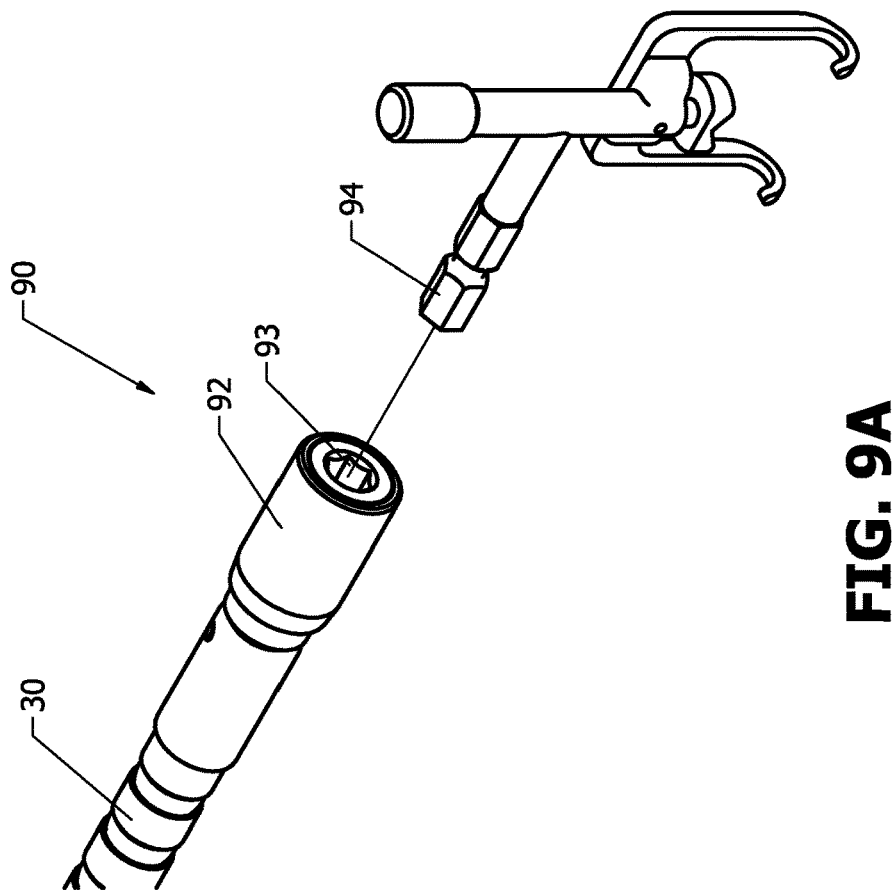

FIGS. 9A and 9B show another connection mechanism 90 that is a quick connect connection mechanism. In this embodiment, a quick connect collar 92 is positioned on the end of the table mounted flexible arm 30 and has a receiving aperture 93. A connector 94 that is geometrically sized and shaped to fit into receiving aperture 93 is positioned off the back of the sheath holder 10 such that insertion of the connector 94 into the aperture 93 (and with actuation of the collar 92) locks/secures the sheath holder 10 into the end of the flexible arm.

Figures 10A, 10B:
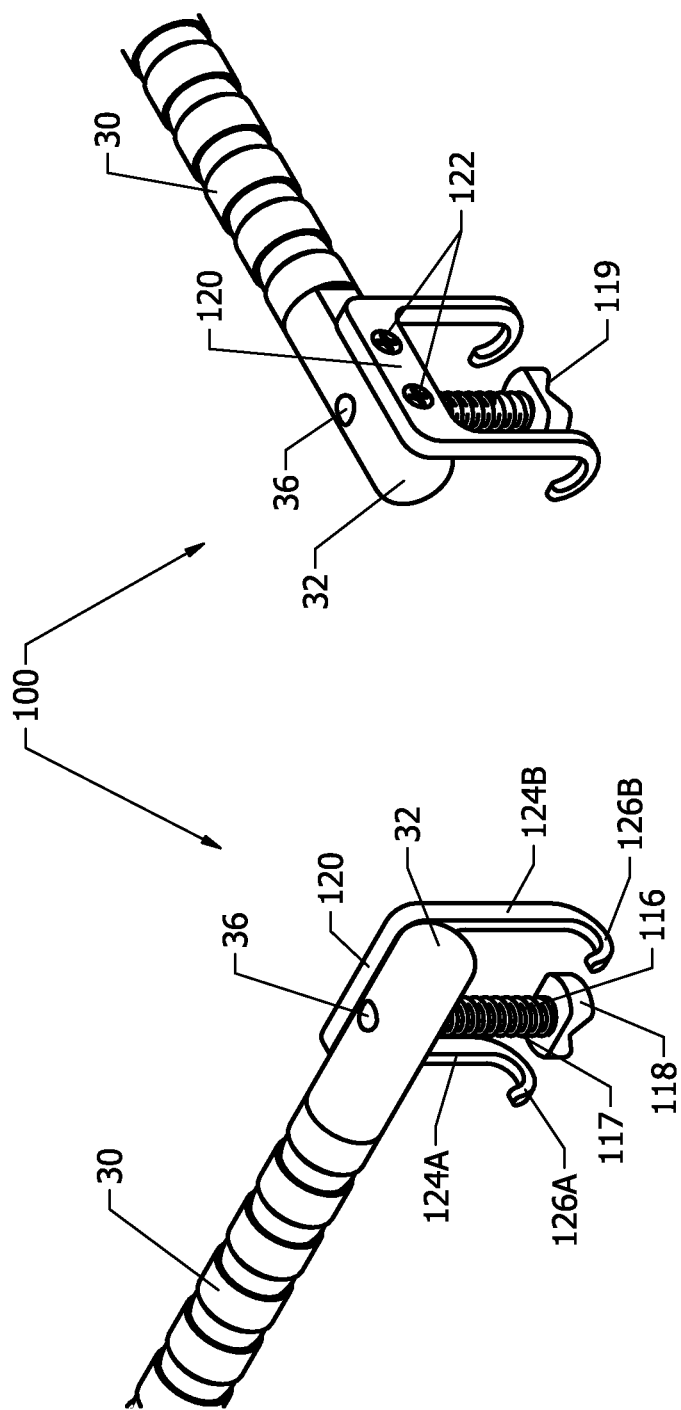
FIGS. 10A and 10B show an alternative implementation where the table mounted flexible or rigid arm is dedicated for use with an integrated scope sheath and holding tip stabilization system according to another embodiment of the invention.

FIGS. 10A and 10B show an alternative embodiment of the sheath holder 10 according to yet another embodiment of the invention. In this embodiment, the table mounted flexible or rigid arm engaging portion and the sheath engaging portion 120 are one in the same and is configured to be fastened directly to an end 32 of the table mounted flexible arm 30 with screws 122, and includes legs 124A and 124B, with hooks 126A and 126B respectively. The plunger assembly includes a shaft 116 with a spring 117 positioned around the same. At the bottom of the plunger shaft 116 is the foot 118 with the beveled or curved surface 119. A hole 36 is provided at the top of the flexible arm to allow the shaft 16 to pass therethrough when pushed upward against the downward spring bias. This embodiment is an example of a dedicated tip style for a flexible or rigid arm.

The above invention has been described in the context of cystoscopy and the use of a cystoscope, however, it is to be appreciated that the concepts and novel structures shown and described herein can be applied to other types of procedures and/or scope/scope sheath configurations. By way of one example, hysteroscopy could be another context within which the concepts and principles of the present invention apply to the scope sheath used for the same. Endoscopy can also be another context for the present invention. The continued intended purpose to stabilize the scope sheath for use by the operating room personnel in such that safety and accuracy can be maintained at all time.

It should also be understood that the example embodiments disclosed and taught herein are susceptible to numerous and various modifications and alternative forms. Thus, the use of a singular term, such as, but not limited to, "a" and the like, is not intended as limiting of the number of items. Furthermore, the naming conventions for the various components, functions, parameters, thresholds, and other elements used herein are provided as examples, and can be given a different name or label. The use of the term "or" is not limited to exclusive "or" but can also mean "and/or".

While there have been shown, described and pointed out fundamental novel features of the present principles, it will be understood that various omissions, substitutions and changes in the form and details of the methods described and devices illustrated, and in their operation, may be made by those skilled in the art without departing from the spirit of the same. For example, it is expressly intended that all combinations of those elements and/or method steps which perform substantially the same function in substantially the same way to achieve the same results are within the scope of the present principles. Moreover, it should be recognized that structures and/or elements and/or method steps shown and/or described in connection with any disclosed form or implementation of the present principles may be incorporated in any other disclosed, described or suggested form or implementation as a general matter of design choice. It is the intention, therefore, to be limited only as indicated by the scope of the claims appended hereto.

Having described preferred embodiments, which serve to illustrate various concepts, structures and techniques that are the subject of this patent, it will now become apparent to those of ordinary skill in the art that other embodiments incorporating these concepts, structures and techniques may be used. Additionally, elements of different embodiments described herein may be combined to form other embodiments not specifically set forth above.

What is claimed is:

1. A scope sheath stabilization system comprising:
    a connection portion configured to securely attach the scope sheath stabilization system to a table mounted flexible or rigid arm; and
    a scope sheath engaging portion connected to the connection portion and comprising
        an inverted U shape device having a top portion and two downward extending legs, each leg having a hook positioned at a bottom thereof, the hooks being configured to be positioned under and engage an underside of the scope sheath; and
        a plunger mechanism extending downward from the top portion and configured to engage an upper surface of the scope sheath.

2. The scope sheath stabilization system of claim 1, wherein the connection portion comprises:
    a shaft having one or more connection points configured to attach the shaft to the scope sheath engaging portion, the shaft being configured to be releasably and securely received by the table mounted flexible or rigid arm.

3. The scope sheath stabilization system of claim 1, wherein the connection portion comprises a shaft having one or more connection points configured to attach the shaft to the scope sheath engaging portion, and wherein the plunger mechanism is spring biased to engage the upper surface of the scope sheath.

4. The scope sheath stabilization system of claim 1, wherein
the plunger mechanism includes a foot configured to engage the upper surface of the scope sheath.

5. The scope sheath stabilization system of claim 1, wherein the hooks are further configured to be positioned under an inflow and an outflow port, respectively, of the scope sheath.

6. A scope sheath stabilization system comprising:
a connection portion configured to securely attach the scope sheath stabilization system to a table mounted flexible or rigid arm; and
a scope sheath engaging portion connected to the connection portion and configured to engage a scope sheath from both an underside thereof and an upper surface thereof to secure the scope sheath from movement once positioned in the scope sheath engaging portion;
wherein the connection portion comprises a shaft having one or more connection points configured to attach the shaft to the scope sheath engaging portion, the shaft being hollow and housing a spring biased plunger mechanism configured as part of the scope sheath engaging portion that engages an upper surface of the scope sheath.

7. The scope sheath stabilization system of claim 6, wherein the scope sheath engaging portion comprises:
an inverted U shape device having a top portion and two downward extending legs, each leg having a hook positioned at a bottom thereof, the hooks being configured to be positioned under and engage an underside of the scope sheath.

8. The scope sheath stabilization system of claim 7, wherein the hooks on each of the downward extending legs are further configured to be positioned under an inflow and an outflow port, respectively, of the scope sheath.

9. The scope sheath stabilization system of claim 6, wherein the plunger mechanism includes a foot configured to engage the upper surface of the scope sheath.

* * * * *